United States Patent [19]

Wilks et al.

[11] 4,377,238
[45] Mar. 22, 1983

[54] FLAW DETECTION AND EVALUATION

[75] Inventors: Robert S. Wilks; Robert H. Sturges, Jr., both of Plum, Pa.

[73] Assignee: The United States of America as represented by the United States Department of Energy, Washington, D.C.

[21] Appl. No.: 181,567

[22] Filed: Aug. 27, 1980

[51] Int. Cl.³ ............................................. B07C 5/342
[52] U.S. Cl. .................................. 209/587; 209/564; 250/223 R; 356/237; 356/426; 358/106; 364/507
[58] Field of Search .......................... 209/562–564, 209/576, 577, 579, 585, 587; 250/223 R, 562, 563, 572; 356/72, 237, 426; 364/507, 522; 358/106

[56] References Cited

U.S. PATENT DOCUMENTS

| | | | |
|---|---|---|---|
| 3,097,743 | 7/1963 | Scholten et al. | 209/577 X |
| 3,221,152 | 11/1965 | Jones | 364/552 |
| 3,282,116 | 11/1966 | Jones | 209/555 X |
| 3,799,682 | 3/1974 | Colestock et al. | 356/237 |
| 3,967,114 | 6/1976 | Cornillault | 250/572 X |
| 4,143,770 | 3/1979 | Grimmell et al. | 356/237 X |
| 4,162,126 | 7/1979 | Nakagawa et al. | 356/237 |
| 4,166,541 | 9/1979 | Smith | 209/587 |
| 4,219,277 | 8/1980 | Yaroshuk et al. | 356/237 X |
| 4,308,959 | 1/1982 | Hoover et al. | 209/587 |

Primary Examiner—Joseph J. Rolla

[57] ABSTRACT

The invention provides a method of and apparatus for optically inspecting nuclear fuel pellets for surface flaws. The inspection system includes a prism and lens arrangement for scanning the surface of each pellet as the same is rotated. The resulting scan produces data indicative of the extent and shape of each flaw which is employed to generate a flaw quality index for each detected flaw. The flaw quality indexes from all flaws are summed and compared with an acceptable surface quality index. The result of the comparison is utilized to control the acceptance or rejection of the pellet.

13 Claims, 10 Drawing Figures

FLAW DETECTION AND EVALUATION

GOVERNMENTAL CONTRACT CLAUSE

The invention herein disclosed was made in the course of or under a contract or subcontract thereunder with the Department of Energy bearing No. EY-67-14-C-2170.

CROSS-REFERENCE TO RELATED APPLICATIONS

This application relates to and incorporates by reference:

1. Application Ser. No. 136,122, field Mar. 31, 1980, to Robert S. Wilks, Robert H. Sturges, and Alexander Taleff for "Pellet Inspection Apparatus" and assigned to Westinghouse Electric Corporation (herein called Wilks I).

2. Application Ser. No. 171,606, filed July 22, 1980 to Robert S. Wilks, Gerald D. Breaky, Eli Sternheim, Alexander Taleff, Robert H. Sturges, and Raymond A. Castner for "Apparatus and Method for Classifying Fuel Pellets for Nuclear Reactor" and assigned to Westinghouse Electric Corporation (herein called Wilks II).

Wilks I relates to the mechanical handling and gauging system for depositing pellets one-by-one in inspection stations and inspecting each pellet for diameter, flaws, length and weight. Wilks II relates to the control for the mechanical handling and gauging system for controlling the depositing of the pellets in the inspection station and their inspection and the processing of the data derived from the inspection. This application relates to the quantification of the flaws, the high-precision derivation of the resulting flaw data and its evaluation.

BACKGROUND OF THE INVENTION

This application relates to the art of inspection and sorting of fuel pellets for a nuclear reactor and has particular relationship to the inspection of such pellets for surface flaws and to the evaluation of the flaws on the surfaces of the pellets for the purpose of classifying the pellets. While this application, including its claims, is confined to the processing of fuel pellets for a nuclear reactor, it is to be understood that to the extent that this invention is applicable to the processing of other articles than fuel pellets, such processing is within the scope of this invention.

The pellets whose inspection and classification are the subject of this invention are relatively small cylinders, typically $0.1945 \pm 0.002$ in diameter, $0.2425 \pm 0.020$ in length and having a weight of $1.204 \pm 0.250$ grams and a specific gravity of 10.22. For use in a nuclear reactor a number of these pellets are stacked in a tube of stainless steel or ZIRCALOY alloy to form a fuel rod. The tube is referred to as cladding. For efficient operation of a nuclear reactor and the precluding of hot spots in the reactor, particularly at the start of operation, it is essential that the heat generated in the pellets flow directly and uniformly to the cladding. It is also essential that the fracture or pulverization of the pellets be avoided during loading of the pellets into the cladding tubes. Surface flaws, depending on their shape, tend to cause non-uniform and indirect flow of heat to the cladding and fracture or pulverization of the pellets.

Flaws may be classified as chips and cracks or fissures. A chip is a flaw for which distances between different sets of opposite points of the perimeter are appreciable compared to the dimensions of the pellet and are of reasonably comparable magnitude. A fissure is an elongated flaw whose length is substantially greater than its width. The distinction between a chip and a fissure is subjective. A narrow chip may be regarded as a fissure and a wide fissure as a chip. However, there are surface flaws which are clearly chips and surface flaws which are clearly fissures.

Where a pellet is chipped, the air or space gap between the surfaces of the chip and the cladding is longer than the gap between the surrounding unflawed surface of the pellet and the cladding. Heat which normally flows from the pellet surface to the cladding now encounters a higher thermal resistance path between the surface of the chip and the cladding and seeks an alternate path around the chip. The path which this flow takes around the chip is shared with the heat from the adjacent unflawed portions of the pellet. A hot ring is developed on the pellet surface around the chip and also on the adjacent cladding wall. The average reactor core operating temperature must be decreased to prevent the hot ring which is developed from rising to a temperature which exceeds the safe design temperature for the cladding and can lead to puncture of the cladding. Reduced average core temperature results in reduced thermal efficiency and power generation capacity. Pellets with severe deep or long fissures may fracture and jam while being loaded in the cladding tubes. This may also occur in the case of chips.

To eliminate or at least reduce the number of flawed pellets in an operating reactor and the problems which they raise, the practice in accordance with the teachings of the prior art has been to inspect the pellets manually.

In accordance with common prior art practice, a pellet passed inspection if it met all of the following criteria:

1. The maximum dimension across a chip does not exceed a specified magnitude.

2. The summation of those maximum dimensions across all chips on a pellet which are greater than an inappreciable predetermined magnitude does not exceed another specified magnitude.

3. Fissures do not exceed a specified length.

The inspection task is formidable. A commercial power reactor having an output of 1200 megawatts thermal energy requires about 10 million pellets. To make available this many pellets in a reasonable time demands a large number of inspectors who must inspect the pellets at a high rate. Typically 100 to 200 pellets are deposited on their sides in a grooved tray and examined by the inspector. After mentally noting the degree of fissuring and chipping on each of 100 to 200 pellets, the inspector places a second tray upside down on the first tray and inverts both trays thus turning the pellets over. He now examines the reverse side of the pellets. The inspector then mentally totalizes the damage on each pellet and sorts the pellets into categories according to the observed surface damage. This task is taxing on the memory and judgement capability of the inspector and is nerve-wracking. Another disadvantage of this manual process is that it is applicable only to pellets of weak radiation emitting material such as uranium. It is not applicable to plutonium pellets which cannot safely be handled manually.

For limited use, for example for test reactors, plutonium pellets are inspected in a glove box one-by-one.

Two persons are required, one picks up each pellet with tweezers and examines it; the other records the data.

A further disadvantage of the prior art is that the above-listed criteria are not satisfactorily correlated to the pellet performance. For example, a circular chip of maximum passable diameter will produce a more severe hot spot than a chip of the same area which is longer but narrower. If the circular flaw were the only flaw on a pellet, criterion 2 above would pass the pellet containing this chip but would reject a more acceptable pellet having the longer narrower chip.

It is an object of this invention to overcome the drawbacks, disadvantages and difficulties of the prior art and to provide apparatus for reliably inspecting for surface flaws fuel pellets for a nuclear reactor at a high time rate such that the large number of pellets required for a typical commercial reactor can be made available within a reasonable time interval. It is also an object of this invention to provide a method for carrying out such inspection in whose practice the surface quality of each pellet shall be quantitatively evaluated in such manner that it is accurately correlated to pellet performance.

SUMMARY OF THE INVENTION

Wilks I and II disclose apparatus including a plurality of stations in which individual pellets are subject to inspection for diameter, flaws, length and weight at a high time rate. Each pellet is advanced automaticaly from station to station during successive cycles and during each cycle all pellets in the stations are inspected. This apparatus operates in a containment so that the inspection and sorting of plutonium pellets presents no safety problem.

For flaws the inspection is effected by scanning successive elemental areas of each pellet with a light beam and determining the surface quality from the transitions in the resulting light reflected from the elemental areas as the incident light passes from unflawed surface areas to flawed surface areas and vice versa (Wilks II—FIGS. 28, 29, 30, 31).

In accordance with this invention, a unique optical system is provided for impinging on the pellet a sharp scanning beam of small dimensions. The scanning is produced by a prism which is rotated at a high speed about a vertical axis. A cylindrical lens interposed in a light beam on the incident side of the prism produces a fine-line vertical image just beyond the prism. As the beam passes through the successive faces of the prism, this image is swept horizontally. A second cylindrical lens interposed between the prism and the pellet focuses the fine-line image on the surface of the pellet. Since the distance between this second lens and the pellet surface is relatively short the image on the pellet is very fine and sharp. A third cylindrical lens, whose optic axis is at right angles to the axes of the first and second lenses converges the line image near the scanning prism vertically to produce an image of very small dimensions horizontally and vertically on the pellet. This image scans the pellet and the resulting reflected light serves to indicate the surface quality of the pellet at each elemental area. Typically, each elemental area is about 0.006 inch in width and height.

The pellet is rotated as it is scanned. The pellet drive is synchronized with the drive for the scanning prism in accordance with this invention. The pellet drive is energized from a 60 Hertz commercial supply. The drive for the scanning prism is of higher frequency and it is energized from a voltage-controlled oscillator (VCO). The synchronization of the drives is effected by controlling the voltage of the VCO in accordance with the phase relationships of the supplies for the drives.

The optical system also includes a ruled grating coordinating each resulting light value with the address on the pellet of the elemental area from which it is required. Light is impinged on the grating by a beam splitter interposed in the beam between the scanning prism and the pellet surface. This light is focused on the grating and as it sweeps across the grating during each scan, it produces a train of pulses. Specifically, the beam splitter is interposed between the pellet and the nearest to the pellet of the second and third cylindrical lenses and the optical distance between the beam splitter and the grating is equal to the optical distance between the beam splitter and the pellet surface. There is then a one-to-one relationship between the positions of the scanning image on the pellet surface and the position of the scanning image on the grating.

The data derived from the scanning of each pellet is fed into and processed by a computer. The memory of the computer is programmed so as to quantize and evaluate the effect on the performance of the pellet, of each flaw. The evaluation takes into consideration the individual shape of the flaw. To each flaw, a flaw quality index FQI is assigned. This is essentially a number depending on the dimensions of the flaw and on its shape. The dimensions and shape are expressed as a shape factor S, F is a function of S. The surface quality of a pellet is expressed as a number, referred to as surface quality index, SQI. SQI is the sum of all flaw quality indexes F for the pellet. In setting up this summation each flaw quality index is weighted based on its shape and on its location, whether it is at an end of a pellet or on the surface between the ends, so that its contribution in the summation is proportional to its contribution to the degree of performance of the pellet in the reactor. In other words F is included in the summation to derive SQI in such a way as to distinguish effectively between the effects on performance of circular flaws, long-narrow flaws and flaws which in varying degrees have shapes intermediate between circular and long-narrow and also in the location of the flaw.

BRIEF DESCRIPTION OF THE DRAWINGS

Figure 1:
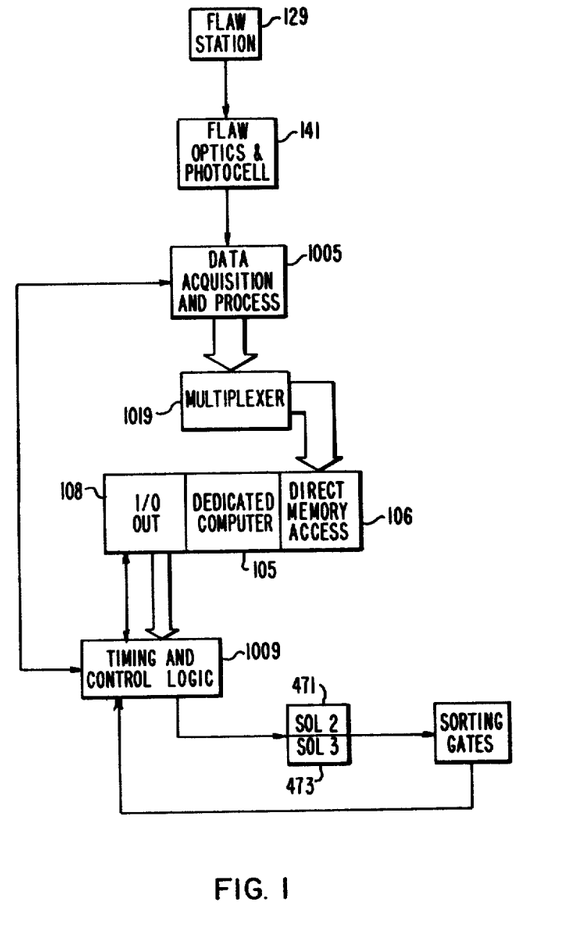
FIG. 1 is a block diagram showing the components of the flaw detection apparatus in accordance with this invention and their relationship.

For a better understanding of this invention, both as to its organization and as to its method of operation, together with additional objects and advantages thereof, reference is made to the following description taken in connection with the accompanying drawing, in which:

FIG. 1 is derived from FIG. 1 of Wilks II and constitutes the portion of FIG. 1 of Wilks II which involves detection and evaluation of surface flaws.

Figure 2:
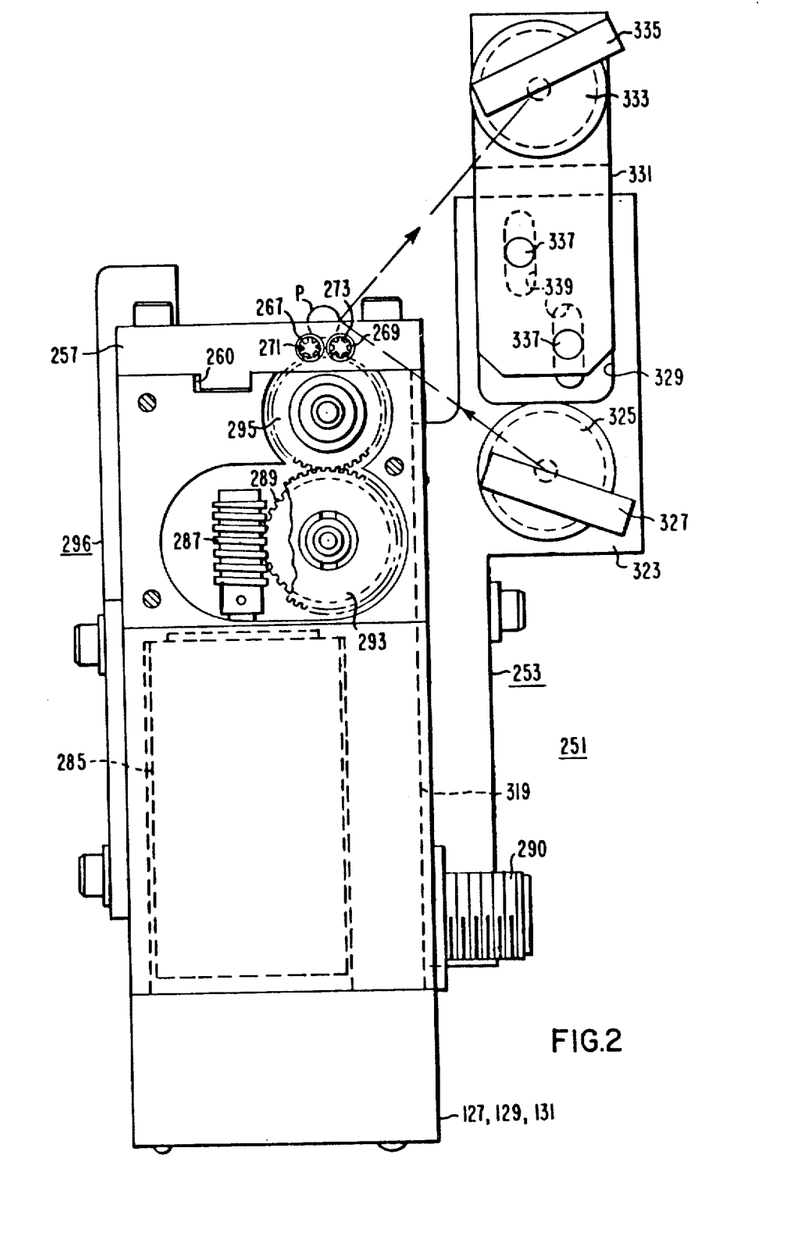
FIG. 2 is an end view of the flaw station in which a pellet is subjected to inspection for flaws.

FIG. 2 is similar to FIG. 47 of Wilks I.

Figure 3:
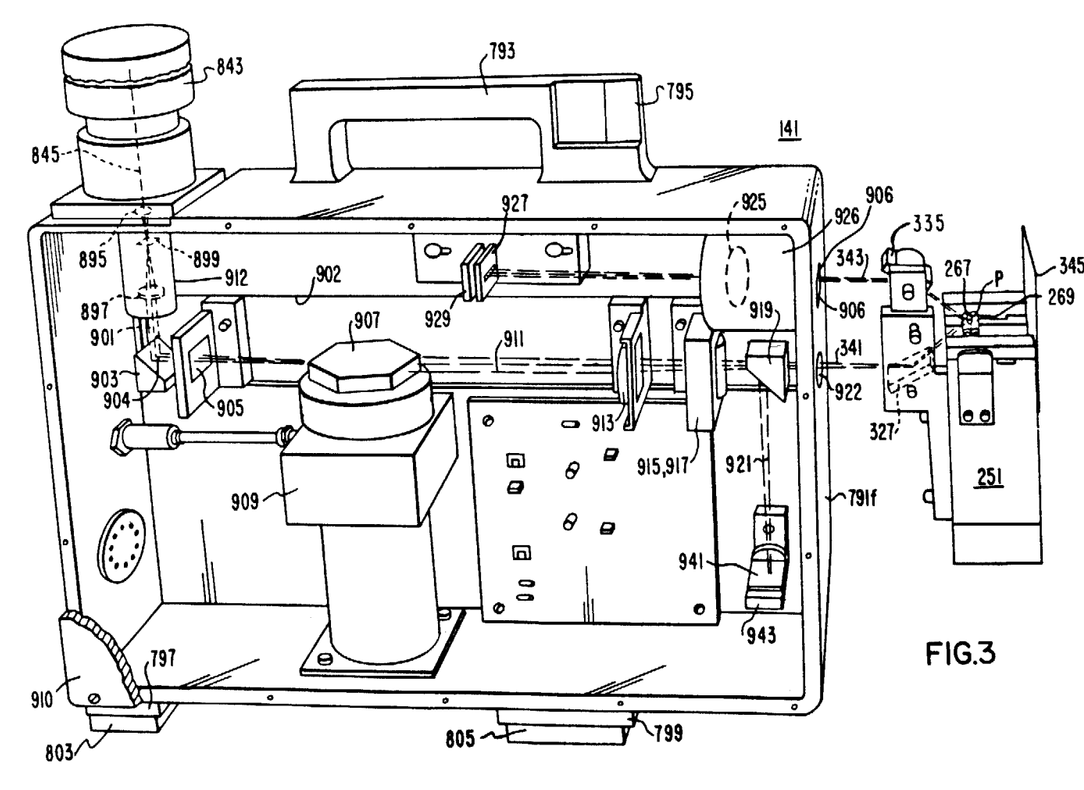
FIG. 3 is a copy of a photograph of the flaw detection optical system of the mechanical handling and gauging system which has been found to be fully operative.

FIG. 3 is similar to FIG. 11 of Wilks I.

Figures 3A, 4:
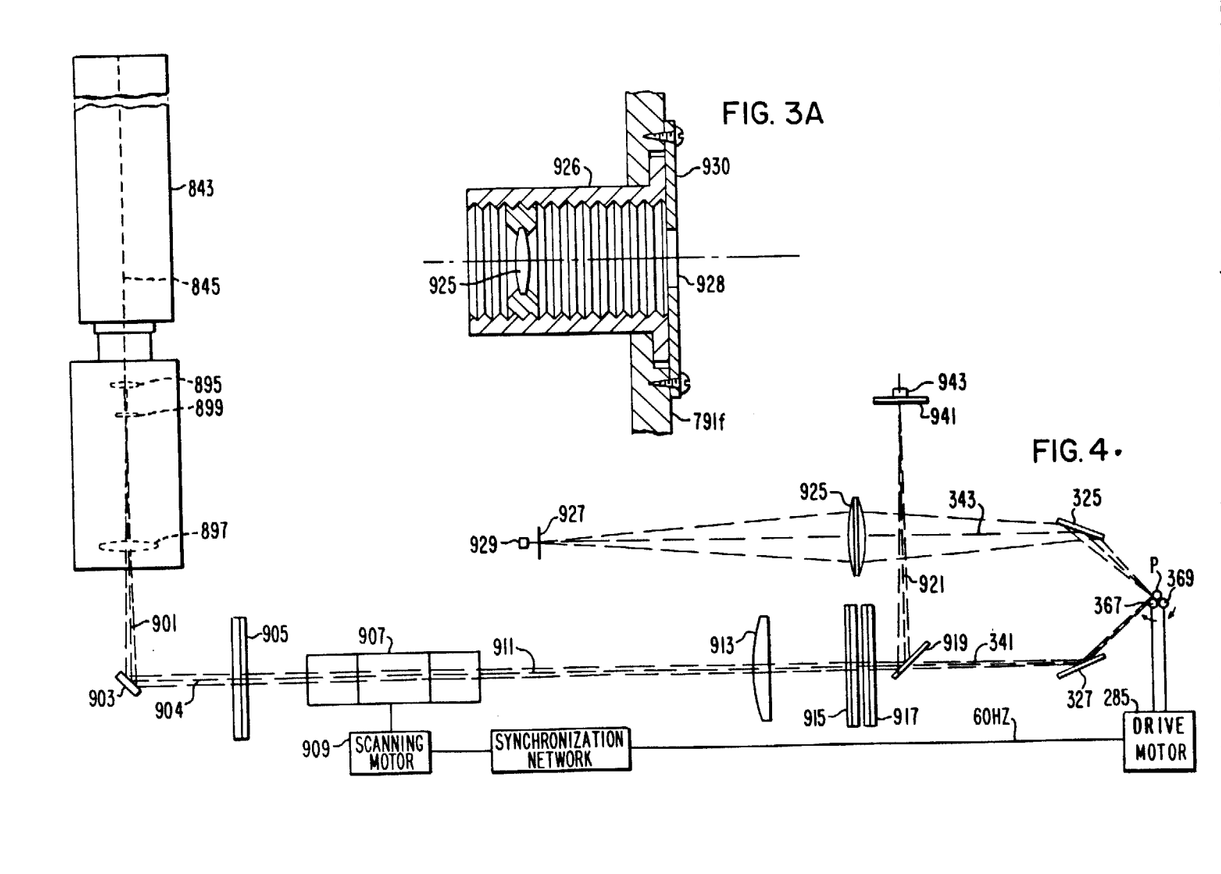
FIG. 3A is a fragmental view in section showing the lens assembly through which the beam from the pellet enters.
FIG. 4 is a diagrammatic view in side elevation of this optical system and also showing in block diagram the drives for the scanning prism and for spinning the rollers on which the pellets are seated and rotated and the synchronization of these drives.

FIG. 4 is derived from FIG. 63 of Wilks I.

Figure 5:
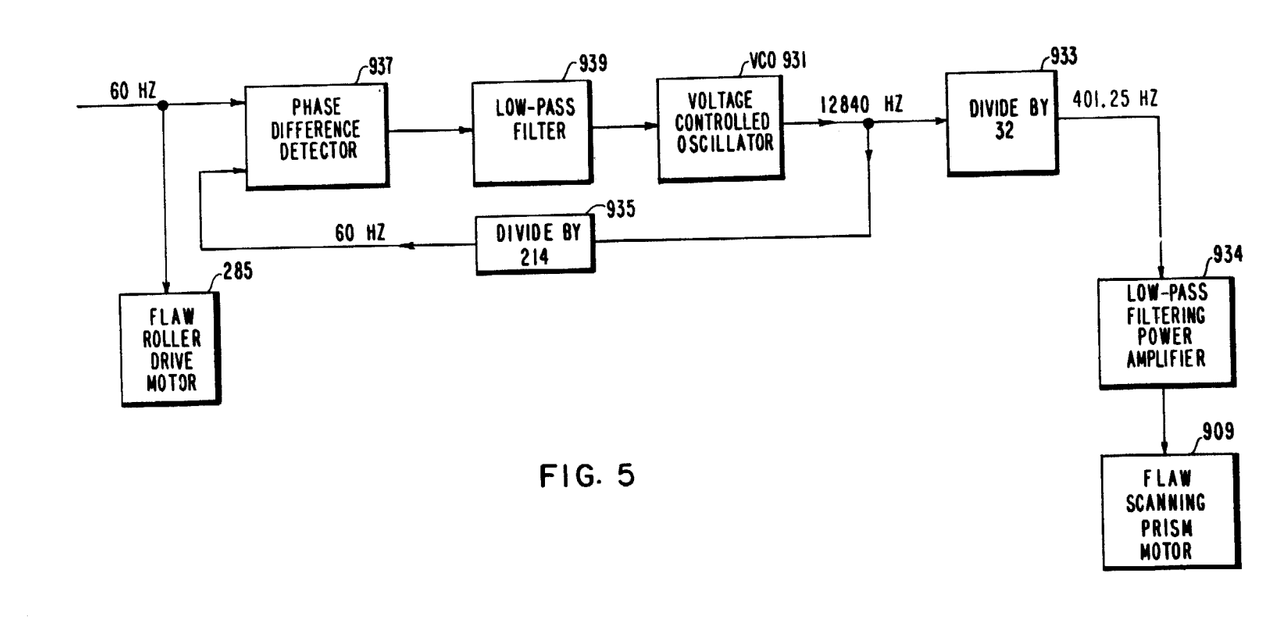
FIG. 5 is a schematic showing the manner in which a pellet spin rate on the roller stand is synchronized with the rotational speed of the scanning prism in flaw inspection.

FIG. 5 is identical to FIG. 13A of Wilks I.

Figure 6:
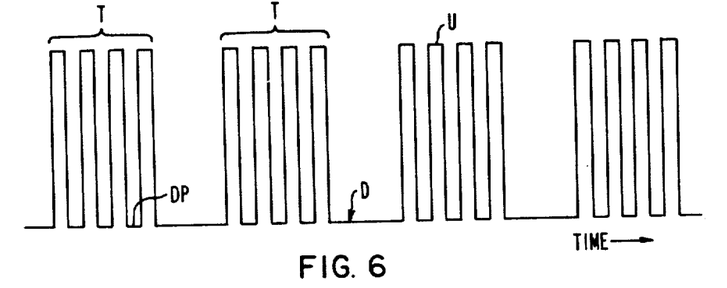
FIG. 6 is a graph showing how the position of the scanning line along the pellet in flaw detection is determined.

FIG. 6 is identical to FIG. 66 of Wilks.

Figure 7:
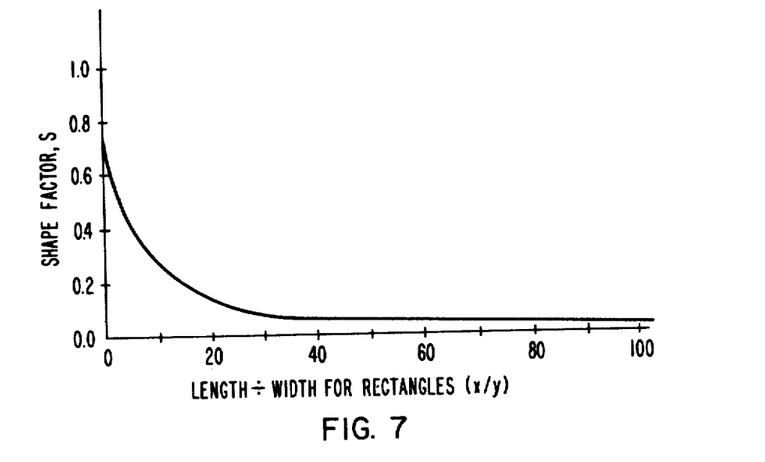
FIG. 7 is a graph which serves to explain how the surface quality index is determined.
Figure 8:
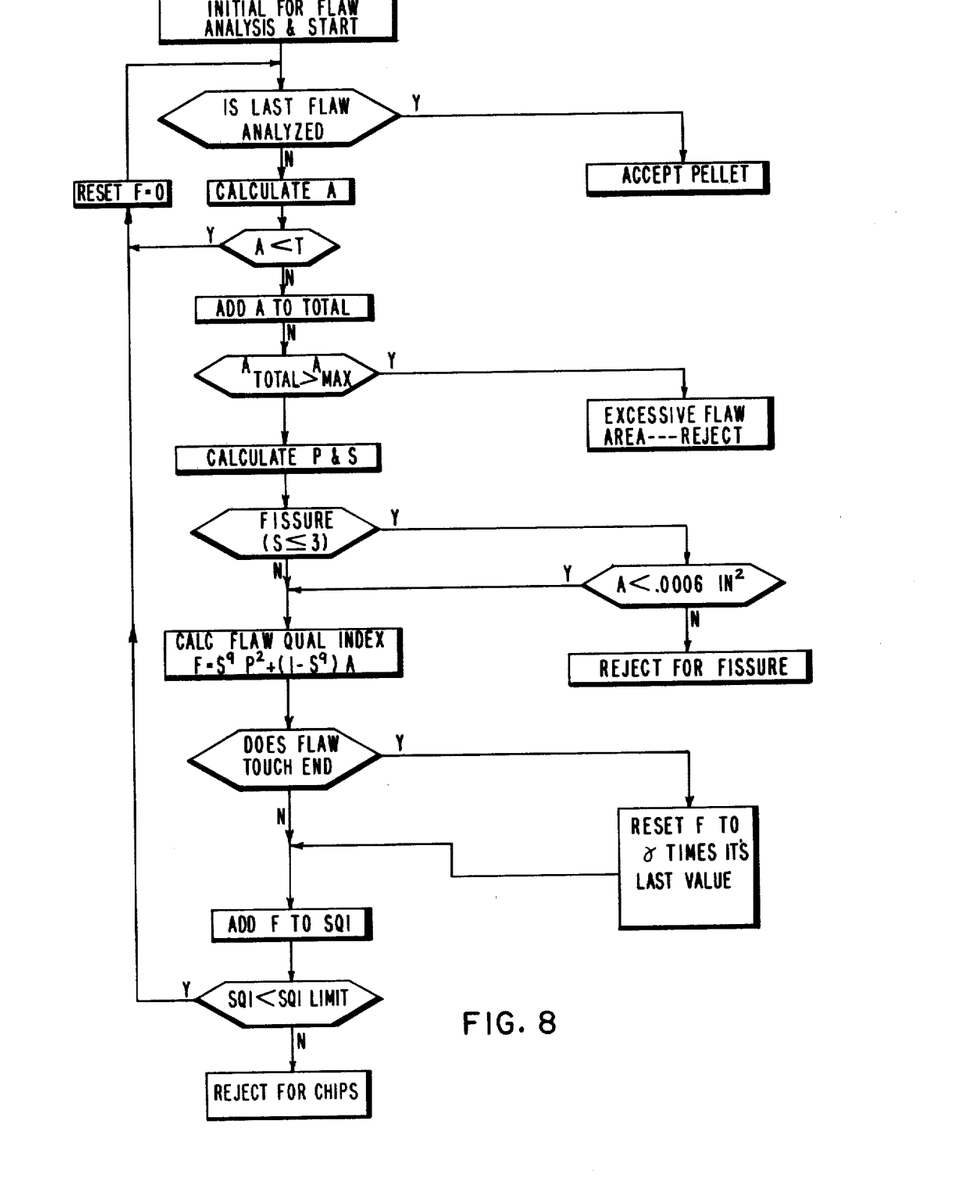
FIG. 8 is a block diagram which shows the algorithm for evaluating fuel pellets with respect to their surface flaws.

FIG. 8 is identical to FIG. 32 of Wilks II except that an error in the latter is corrected. In FIGS. 1, 2, 3, 4, 5 and 7 the numbering of the corresponding Wilks applications is retained.

DETAILED DESCRIPTION OF THE INVENTION

The apparatus shown in FIG. 1 includes a flaw station 129 (FIGS. 2, 3) and the flaw optics and photo cells 141. The block 141 represents the optical system (FIGS. 3 and 4) and the photo-responsive means or photo-cell which produces the counts which evaluate the flawed areas of each pellet. The apparatus shown in FIG. 1 also includes the data acquisition and process 1005. This includes the logic which acquires the data from the photo responsive means and processes this data (Wilks II—FIGS. 28, 29). The data derived from the photo responsive means is entered into a FIFO buffer 1019 (Wilks II, FIG. 2, FIG. 29) and during the MEASEN, the measurement enable interval, is transmitted through multiplexer 1019 (Wilks II—FIG. 37) and through the direct-memory access (DMA) 106 into the dedicated computer 105. The dedicated computer 105 produces a digital image of the pellet surface with its flaws and it determines the dimensions, specifically the area and perimeter, of each flaw. The computer can also produce an actual image of a pellet surface on a cathode-ray screen. The computer 105 also computes the FQI for each flaw and assigns to each flaw a weight to the FQI which is correlated to the degree of performance reduction of the pellet which each flaw, by reason of its particular shape and position, contributes. The computer 105 derives the SQI from the weighted FQI's for each pellet. The computer 105 is in communication with timing and control logic 1009 through its interface board I/O, 108 (Wilks II, FIGS. 42, 43). The board 108, through the timing and control logic 1009, coordinates the flow of data between the data acquisition and process 1005 and the computer 105 through the DMA. It also actuates the timing and control logic 1009 to actuate solenoids 471 or 473 appropriately so that the spring gates are operated in accordance with the evaluation of the flaws (or of the other parameters) of each pellet. The intelligence as to the setting of the sorting gates (through PC4, PC5—Wilks II, FIG. 5, 499–503, 501–505—Wilks I—FIG. 31) is supplied for processing to the timing and control logic 1009. It is to be borne in mind that the blocks of FIG. 1 predominantly define functions and not structure. Structurally, the components of these blocks may be intermingled.

Each pellet P is subjected to inspection in the flaw station 129 on rotating rollers 267 and 269 (FIGS. 2, 3) in a box 251 which is described in more detail in Wilks I (FIGS. 45–47).

The box 251 has a groove 319. A bracket or mounting 253 having a cooperative tongue member is supported in the groove 319 and secured therein. In the lower part of its head 323, the bracket 319 has an adjustable mounting 235 for a plane mirror 327. This mirror is secured in the mounting 325 by tape. The mounting 325 is in the form of a disc and can be adjusted to set the angle of the mirror 327 to the horizontal. In the upper part of this head there is a slot 329. Within this slot a bracket 331 is slidable. At its top the bracket 331 carries an adjustable mounting 333 in the form of a disc. This mounting carries a plane mirror 335 secured therein by tape. The bracket 331 is secured in slot 329 by screws 337 which pass through slots 339 in the head 323. The mirror 335 is adjustable vertically by adjusting the position of the screws 337 in the slots 339. The angle of the mirror 335 to the horizontal is adjustable by mounting 333. The mirror 327 is so set that this mirror reflects a horizontal scanning beam 341 (FIGS. 3, 4) having the contour of a sharp spot tracing a horizontal line from the source and optical system 141 to the surface of a pellet P on the seat formed between rollers 267 and 269 at the flaw station. The reflected beam scans the surface of the pellet P. Specular or unflawed surface elements of the pellet P reflect the beam to the reflector 335. This reflector is so set that it reflects the scanning beam 343 (FIGS. 3, 4) horizontally to the source and optical system 141.

The box 251 at the flaw station 129 is provided with a plate 345 (FIG. 3). The plate 345 is secured to the rear wall of the box and extends completely across the deep opening of the box. The purpose of the plate 345 is to shield persons facing the apparatus from the laser beam projected towards the flaw station 129.

The flaw inspection optical system (FIGS. 3 and 4) except for mirrors 327 and 329 is mounted in a container 791f. This container is similar to the containers for diameter and length inspection which are described in Wilks I. The container 791f is generally like a suitcase having a handle 793. A locating plate 795 extends from the handle 793 on one side. The function of this handle 795 in positioning the container 791f vertically is described in Wilks I.

A laser beam 845 derived from a laser in the top of tube 843 is collimated and polarized and is projected through a telescope including lenses 895 and 897. Interposed between lenses 895 and 897 is a pin-hole filter 899 having a pin-hole about 35 microns in diameter. Lens 895 focuses the light on the pin-hole; lens 897 collimates the light. The beam 901 which emerges is magnified by six diameters with reference to the beam 845. This beam is reflected by plane mirror 903 so that a horizontal beam 904 is produced. Beam 904 is incident on cylindrical lens 905 which converges the beam horizontally into a thin vertical line real image. The converging beam from lens 905 is incident on scanning prism 907 which is rotated at a high speed, typically 7000 RPM, by motor 909. The beam which emerges from cylindrical lens 905 is focused as a line image a short distance in front of scanner 907, i.e., beyond the scanner 907 along the path of propagation of the beam. Scanner 907 produces a scanning beam 911 whose cross-section is a thin vertical line. Beam 911 sweeps horizontally while remaining parallel to the optic axis of lens 905. Beam 911 passes through cylindrical lens 913 whose axis of curvature is horizontal. Lens 913 converges beam 911 vertically to a sharp point. This point, i.e., the conjugate focal point of lens 913 is on the surface of pellet P. The beam from lens 913 is incident on cylindrical lenses 915 and 917 which operate as a single lens. The beam which emerges from lenses 915 and 917 is converged horizontally and also focused on the surface of pellet P. Lenses 915 and 917 cooperate to produce a sharper line on pellet P than would be produced by lens 905 or a plurality of lenses in this area. Essentially lenses 913, 915, 917 produce an image of the real image beyond scanner 907 at the surface of the pellet P.

The minimum spot area (or line width for a cylindrical lens) producible from a collimated beam by a lens is diffraction limited; the larger the angle of convergence, the smaller this spot area. The focal length of lens 905 could have been selected to focus the beam directly on the pellet. But under such circumstances the spot line width would have been greater than desired. The cooperation of lenses 905, 915 and 917 makes it possible to maintain the angles of convergence and divergence to and from the lenses large enough to insure a small width as desired at the pellet surface. By providing convergence in the vertical optical axis after prism 907 by means of lens 913 the system is rendered immune to precession errors introduced in the mounting of prism 907.

The beam emerging from lenses 915 and 917 is incident on a beam splitter 919 disposed at an angle of about 45° to the axis of the beam. Part of the incident beam passes through the beam splitter and emerges as beam 341. The other part of the beam is reflected vertically (actually downwardly—FIG. 3) as beam 921.

Beam 341 passes through a window 922 in container 791f, is reflected by mirror 327 on the roller stand 251 at the flaw inspection station 129 and is focused as a fine sharp point on the pellet P. As the scanner 907 rotates, this line scans the pellet P. Mirror 335 reflects the light from the spot as horizontal beam 343 through another lens 925 adjustably secured in a barrel 926 (FIG. 3A) in container 791f axially aligned and penetrated by the beam 343. The beam 343 enters barrel 926 through a slot 928 in a baffle 930 (FIG. 3A). Lens 925 focuses the spot from the pellet on a baffle 927 having a narrow horizontal slit. The light passing through the slit is incident on a photocell or photo responsive device 929. The slit in baffle 927 and photocell 929 are so set with reference to beam 343, that light undergoing reflection at the surface of the pellet P passes through the slit onto the photocell 929. Light derived from a flaw in the surface of pellet P is focused as an image away from the slit and is intercepted by the wall of the baffle 927. In addition the surface of the flaw being less mirror-like than the unflawed surface diffuses the light. In either event there is for a flaw a substantial decrease in the photon energy impinging on the photocell which is an indication that the surface under the spot at the pellet surface is not unflawed.

The rollers 267 and 269 on which the pellet is seated is driven by the synchronous motor 285 at a substantially lower speed than the scanner 907. Typically the pellet rotates at about 629 RPM. The pellet length is then scanned anew for each small incremental movement of the pellet circumference. The scanning traces a screen of imaginary rectangles on the pellet surface which envelops the pellet surface. The imaginary rectangles of the imaginary screen which envelops the pellet are of small area, typically 0.006 inch square.

The scanning motor 909 is driven from a voltage-controlled oscillator (VCO) 931 (FIG. 5). Typically the VCO 931 has a center frequency of 12,840 Hertz. The motor 909 is supplied from VCO 931 through a divider 933 which typically divides by 32 and a low-pass filtering power amplifier 934 to preclude frequencies appreciably higher than 401.25 Hz. The motor 901 operates at a speed typically at 8025 RPM. The roll motor 285 in the flaw detection stand 251 at station 129 which is synchronous is supplied from a commercial 60 Hertz source. The 60 Hertz source is also connected to a phase-difference detector. The output of VCO 931 is also supplied through the second divider 935 to a phase-difference detector 937. The dividing factor of divider 935 is such that the signal flowing to the phase detector 937 is a 60 Hertz signal. The output of the phase detector 937 supplies synchronizing voltage to VCO931 through a low-pass filter 939. Thus prism motor 909 and roller motor 285 are synchronized since both are supplied basically from the same commercial 60 Hertz service and are maintained in synchronous by the phase-difference detector 937.

The vertical beam 921 (FIGS. 3, 4) serves to provide information of the relative position on the imaginary grid of the light spot on the pellet P. Since the beams 341 and 921 are derived from a common beam focused by lenses 913, 915, 917, the conjugate focal point of beam 921 as it sweeps is at each instant the same distance from the optical center of the beam splitter 919 as the light spot on the surface of the pellet as it sweeps across the surface; i.e., the optical path distances from the reflective surface of the beam splitter to the spot in the surface of the pellet and to the conjugate focal spot of the split-off beam of 921 are equal. There is then a one-to-one correspondence between the relative positions of the two spots. A Ronchi ruling 941 is placed at the conjugate focal point of beam 921. Ruling 941 is a grating on which lines are ruled. A photocell 943 is mounted behind the Ronchi ruling 941. The light emerging from the ruling 941 causes the photocell 943 to produce successive trains T of current pulses U as shown in FIG. 6. The dimension of the Ronchi ruling 941 perpendicular to the lines is larger than the longest pellet to be subject to inspection to allow for scanning over the ends of the pellet (as well as for pellet positioning tolerances). This dimension is shorter than the length of the scan so that there is a short period of darkness between scans. This darkness interval is identified by D in FIG. 6.

Each train T corresponds to a scan of the length of pellet P and each pulse U in a train corresponds to a position along the length of the imaginary screen which is being scanned. With the pulses derived from photodiode 943 the position of each elemental region of the pellet P scanned can be determined electronically.

Electronic circuitry (FIGS. 28, 29—Wilks II) can determine the position of the beam within a scan by counting the light pulses U since the last pause D. The circuitry detects the end of a scan by detecting that the period of darkness D between trains T is prolonged beyond that corresponding to the duration DP between pulses. Every light pulse corresponds to a discrete address in the imaginary cylindrical grid which envelops a pellet P and rotates with it. At the peak of every pulse U the electronic circuitry examines the output from photocell 929 (FIG. 4) to evaluate the reflection from the spot at the corresponding address. The absence or presence locally of a sound surface is thus determined.

It is essential that the flaw optical system shall be properly aligned. At the outset, it is assured that the drive rollers 267 and 269 are properly aligned with the related components of the mechanical handling and gauging system (101, FIG. 1—Wilks I). It is also assured that the mounting pins, pockets and grooves (FIGS. 13, 14, 15—Wilks I) for mounting the rollers and the suitcase 279f are clean and in proper condition for mounting of these parts.

The laser mount 843, the mount for lens 905, the mount for the scanning prism 907, and the mount for cylindrical lenses 913, 915, 917, and their attached parts are removed from the suitcase 279f. The suitcase 791f is positioned on the inspection system table. The locating buttons (809, FIG. 15—Wilks I) should be set so that the optical mounting racks, the racks such as 902 (FIG. 3) for mounting lenses and other optical components, in suitcase 791f are parallel to the table top and the centerline of the window 922 in the suitcase 791f is a proper distance, typically 1.00 inch below the center line of a nominal pellet P resting on rolls 267 and 269. The suitcase face to which cover 910 bolts should be square with the top and back edge of the table (817, FIG. 4—Wilks I). The buttons or pins (809, FIG. 15—Wilks I) should be secured by Loctite (TM) cement and the plates 803 and 805 should be secured tightly to the suitcase 791f. The outer tube 912 and forward lens 897 of the telescope 895–897 is unscrewed from its spatial filter holder (not shown in detail; it is mounted in the bottom of the laser mount).

The power to the laser is turned on and its mechanical shutter (not shown) is opened. This shutter is accessible through an access hole (not shown) in the laser mount 843. The spatial filter is aligned in accordance with the instructions of Metrologics Instruments, Inc., the manufacturer of the collimating telescope, which is used in this apparatus (Wilks I, page 40). The room should be darkened for this alignment. The outer sleeve 912 of the expanding telescope 895–897 should now be remounted. The sleeve 912 should be seated firmly against the laser mount 843. The forward lens should now be focused so that the beam 901 is collimated. The diameter of the beam 901 should be the same several feet (for example, 3 feet) as it is directly in front of the lens.

The laser assembly and the other parts are remounted in the suitcase 279f. The beam 904 (FIG. 3) reflected from mirror 903 should be parallel to the optical mounting tracks 902. Typically, the beam 904 should be a distance of 1.625 inches horizontally from the tracks and a distance of 1.125 inches above the lower edge of the lower track. The appropriate setting is achieved by adjusting the laser mount 843 laterally (within the play of its mounting screws) and by adjusting the mirror 903 backward or forward or angularly. If rotation of the mirror 903 about the vertical axis is required, it will be necessary to shim the base (not shown) of the mirror at the forward or backward end. If the parts are properly adjusted, the beam 904 emerges from suitcase 791f through the center of the window 922.

The mounts for lenses 905, 913, and 915–917 and their lenses and associated parts are replaced. If the parts are properly replaced, the beam, now 341 (FIGS. 3, 4), emerges through the center of window 922. If the beam 341 is high or low it is set by shimming the mount for lens 905. If the beam 341 is shifted horizontally, it is set by shimming either or both lenses 913 and/or 915, 917.

The scanning prism 907 is replaced. The prism is spun slowly to assure that the sweeping beam 911 scans equal distances either side of the optical center line. The prism 907 may be shimmed as necessary.

Now the seat 267–269 for the pellet P in box 251 is adjusted so that the pellet is properly positioned for flaw inspection. The beam shield 345 is removed and the mount 253 (FIG. 2) is adjusted so that the center line of the mount 325 for the lower mirror is 327 at the same level as the center of window 922; i.e., typically 1.00 inch below the center line of a nominal pellet P on rollers 267 and 269. The slide 331 is adjusted so that the center-to-center distance between mirror mounts 325 and 333 is such that the center of mount 333 is aligned with the center of window 906. (FIG. 3). Typically, the distance between the centers of mirror mounts 325 and 333 should be 2.375 inches. The scanning prism 907 is adjusted so that the center of the scan of beam 341, projected from the suitcase 791f is in line with the normal position of a nominal pellet on the rolls 267–269. The lower mirror 327 is adjusted angularly so that the beam 341 is incident on the pellet P at the elevation of its axis. The vertical spot size is adjusted by moving the mount for lens 905 or the mount for lens 915–917 forward or backward on the optical mounting track.

This spot size can be checked with a 100-line per inch Ronchi ruling (grating). The open spaces between the lines of such a grating is 0.005 inch. The ruling is placed where the scanned spot normally is incident on the pellet P and with its lines horizontal. A piece of paper is held between the grating and the observer. As the grating is moved slowly upwardly while being held in its plane, the light on the paper flickers. The position of the ruling should be positioned where the light has the minimum intensity on the paper. When the spot is of the proper dimensions, there should be substantially no light on the paper. Ronchi rulings of 80 or 133 lines per inch (gap widths of 0.0062 inch and 0.0038 inch) may be used to develop skill and confidence in this practice. The horizontal spot width can be adjusted by moving lens 913 backward and foward using the same technique but with the rulings vertical.

A piece of lens tissue is taped over the baffle 930 (FIG. 3A) in front of the imaging spherical lens 925; i.e., in front of the suitcase 71f. The tissue acts as a viewing screen. The room is darkened and then the upper mirror 335 (FIG. 2) is adjusted angularly to a position at which the light reflected from the pellet is vertically centered on the baffle opening 928. The lower mirror 327 is adjusted to maximize the image brightness. The tissue is then removed from the baffle.

The mounting plate for photocell 929 is adjusted so that the photocell is at its mid position. The slide for the grating 941 and photocell 943 and the slide for the photocell 929 and slot 927 are adjusted until these components are in their mid positions. Lens tissue is taped over the slot 927. The spherical lens 925 is adjusted to sharply focus the reflection from pellet P on the slit 927. Fine focusing can be achieved with an axially oriented slide (not shown). The tissue is removed.

The scanning prism 907 is spun to check that the scanned image is parallel to the slit 927. Adjustment is effected by the slide which holds the slit 927 and photocell 929. The slit 927, which is formed of razor blades, is adjusted to narrow the slit until the light spot nearby is incident on the blades. The vertical slide which holds the grating and photocell is adjusted so that the scanned line image is very near the lower blade.

It is desirable at this point to discuss briefly the difficulties which the aspect of this invention involving the optical system overcomes. The task which gave rise to this invention was the provision of condensing a collimated beam to a sharp scanning spot on a pellet. A way to accomplish this object is to place a convex spherical lens before the scanning prism 907; i.e., between the source and the scanning prism. This lens would produce a light-spot image on the pellet. But this expedient involves at least two drawbacks.

First, the scanning prism cannot be perfectly mounted and it wobbles as it spins. This causes the scanned line upon the pellet surface to be cast at different elevations for successive prism face scans. If the lens were positioned after the prism 907 (instead of before it) the light paths emerging from the prism would still be parallel to the path of the entering light and would therefore converge to the same elevation. The rays would, however, all converge to the same spot and there would be no scan.

The second difficulty has to do with the problem of obtaining a small spot size at the pellet surface. On the one hand, the minimum sized spot to which a lens can converge a collimated beam is inversely proportional to the effective f-number of the lens; in other words, to the diameter of the beam divided by the focal length of the lens. This constraint is imposed by natural laws. On the other hand, the position most appropriate for the spot converging lens is before the scanning prism, but between there and the pellet are the scanning prism and its mount, an instrument case wall, a containment wall, a beam-splitter, a mirror, and the bulk of the stand on which the pellet rests. Space taken up by this gear decidedly limits how close to the pellet the converging lens can be positioned. That in turn limits the minimum spot size to a value which is too great for this application. This invention overcomes the above drawbacks with lens 905 and the interposition of lenses 913 and 915-917.

The computer 105 is programmed to evaluate each pellet in dependance upon the shape and extent of its surface flaws. The quantification of the shapes of flaws in the practice of this invention will now be described. The significant characteristics of a flaw are its area A and its perimeter P. As a basis for quantifying each flaw a dimensionless flaw shape factor, which is a function of A and P, is adopted. The factor S is defined by the equation:

$$S = K \frac{A}{P^2}$$

The value of K is an arbitrary choice. It is selected here so that S is 1 when $A/P^2$ is maximum. $A/P^2$ is a maximum when the defect is circular. Hence $A_o = \pi r^2$ and $P_o = 2\pi r$.

The subscript 0 indicates that the parameter is for a circle.

$$S_o = K \frac{\pi r^2}{(2\pi r)^2} = 1$$

Solving (2) we get $K = 4\pi$. Therefore;

$$S = \frac{4\pi A}{P^2}$$

A criterion which appears in Paragraph 3.7 of the specifications of Hanford Engineering Development Laboratory called for rejection of all pellets containing fissures or cracks extending greater than 180° around a pellet surface or extending greater than 0.100 inch in the axial direction. If such a fissure is to be detectable by a scanning light spot as in this case, it should be about as wide as the spot. A fissure of half that width could absorb only about half the incident light energy. If this were the threshold established to differentiate an acceptable pellet surface from an unacceptable surface, such a flaw would have a 50% probability of detection. By the same argument a fissure having a width equal to the scanned element would have a 100% probability of detection. Since the light intensity distribution of the cross-section of the beam is Gaussian, the detection probability is greater than stated for any fissure except a fissure parallel to the scan.

Suppose there is a fissure which is 0.100 long (shortest rejectable length) and 0.006 wide (the typical diameter for the scanning spot). Its area, perimeter, and S would be as follows:

$$A = (.100 \text{ in}) (.006 \text{ in}) = .0006 \text{ in}^2 \quad (4)$$
$$P = (.100 \text{ in} + .006 \text{ in})2 = .212 \text{ in} \quad (5)$$

$$\frac{(.0006 \text{ in}^2)}{(.212 \text{ in})^2} \times 4\pi = .16776 \text{ (from 3 \& 5)} \quad (6)$$

Experience suggests that fissures and chips are easily discernible to the eye, probably because of the marked difference in their shapes. The inventors cannot recall ever seeing a fissure as wide as a 0.012" nor a chip which was 0.100 long and only 0.012" wide (S for such a chip would be 0.301). Since neither chips nor rejectable fissures appear to occur near S=0.3, a fissure is defined as a flaw with S equal to or less than 0.3. Conversely, any flaw with S>0.3 will be defined as a chip. This should offer a reasonable margin of safety on either side.

The software for flaw detection of this invention does not analyze flaw orientation. To be safe, any fissure longer than 0.100 is a cause for pellet rejection. As a practical matter fissure length can be estimated in either of two ways—by area or by perimeter. A 0.100 inch long fissure with a 0.012 inch width (marginally rejectable) has an area of 0.0012 square inches and a perimeter of 0.224 inch. A fissure with either an area or a perimeter greater than this would be rejected. It is to be kept in mind that the apparatus according to this invention arbitrarily assigns a 0.006 inch width to any detectable fissure narrower than 0.006 inch.

Chips are of concern because heat generated beneath a chip must flow out to the surface regions beyond the chip boundaries before it can be conducted to the cladding. For a small circular chip, it is assumed that the diverted energy is proportional to the flaw area and the pellet surface through which it dissipates if proportional to the chip circumference. The local temperature increase at the flaw circumference would be roughly proportional to the increased heat flux attributed to the flaw; in other words, in ratios of area to circumference $(A \div P)$. For a circular flaw $A \div P = \pi r^2 \div 2\pi r = r/2$. Now, r and P are proportional, therefore, the quality index for quantifying the dimensions of a circular chip should be weighted in direct proportion to its perimeter.

If a chip were infinitely long compared with its width than the heat flux would be two-dimensional rather than three. Using the same reasoning as above the heat flux would increase in direct proportion to the chip width (as would the chip edge temperature). For flaws of infinite (but constant) length the chip width is linearly related to the chip area. It follows that the flaw quality index for quantifying a long narrow flaw should be weighted in proportion to the dimensions of its area.

The flaw quality index of circular flaws should then be based on perimeter, and that of very long flaws should be based on area. For flaws intermediate the long and circular flaws, it would appear reasonable to base the flaw quality index partly on each. How to ration the allocation will now be considered. For determining the allocation, a function $\alpha$ is defined which is called the allocation function. The function has values ranging from unity when $S=1$ to zero when $S=0$. If a flaw has an $\alpha=1$, the flaw quality index, is based 100% on perimeter; if $\alpha=0$, it is based 100% on area. If $\alpha$ is 0.75, the flaw quality index is based 75% on perimeter and 25% on area.

As a practical matter, it is reasonable to assume that when the ratio of length to width of a chip becomes larger than about five to one, the heat flux pattern would become essentially two-dimensional. The allocation function $\alpha$ must yield a result close to zero for this flaw. Furthermore, it must be assymptotic with zero at $S=0$.

S, the shape factor, for a rectangle is very near to what is required for $\alpha$ in accordance with the above analysis. The following Table I presents the data involved in the quantification of rectangular flaws of various dimensions.

TABLE I

| y | x | A | P | $A/P^2$ | $S = 4\pi A/P^2$ |
|---|---|---|---|---------|------------------|
| 1 | 0 | 0 | 2 | 0. | 0. |
| 1 | 1 | 1 | 4 | .0625 | .785 |
| 1 | 2 | 2 | 6 | .0556 | .699 |
| 1 | 5 | 5 | 12 | .0347 | .436 |
| 1 | 10 | 10 | 22 | .0207 | .260 |
| 1 | 20 | 20 | 42 | .0113 | .142 |
| 1 | 50 | 50 | 102 | .0048 | .060 |
| 1 | 100 | 100 | 202 | .0025 | .0308 |
| 1 | ∞ | ∞ | ∞ | 0. | 0. |

Figure 7A:
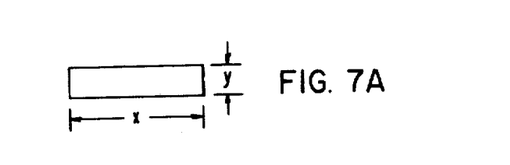
FIG. 7A is a diagram showing the significance of the data in FIG. 7.

The first and second columns from the left tabulate the width of y and the length x of the rectangle of FIG. 7A which represents a flaw. The third and fourth columns present the corresponding areas A and perimeters P, the fifth column $A/P^2$ and 6th column, the shape factor $S=4\pi A/P^2$.

FIG. 7 is a graph based on Table I. The shape factor S is plotted vertically as a function of the length x divided by the width y. This quotient is plotted horizontally. It is seen that S increases as x/y decreases but drops to a low value for magnitudes of x/y above about 16.

It is desirable for proper quantification of flaws that S approach the x/y axis more sharply. To achieve this purpose $\alpha$ is equated to $S^q$, where q is greater than 1.

A value of $q=3$ would yield $\alpha=0.08$ for a rectangle with a length to width ratio of 5. The value of q can be fine-tuned as more is learned about in-core performance of flawed pellets.

Based on the above analysis the flaw quality index F may be derived as follows:

$$F = \alpha P^2 + (1-\alpha)A \quad (8)$$

$$F = S^q P^2 + (1-S^q)A \quad \text{ref. (7) and (8)} \quad (9)$$

$$F = \left(\frac{4\pi A}{P^2}\right)^q P^2 + \left(1 - \left(\frac{4\pi A}{P^2}\right)^q\right) A$$

The surface quality index, SQI, for an entire pellet is the summation of flaw quality indices for all flaws (including fissures) for a pellet.

A criterion adopted by Hanford Engineering Development Laboratory called for rejection of all pellets having two or more flaws each having a major width greater than 0.050 inch. Two circular chips of 0.050 diameter are rejectable under this criterion. This criterion may be established for the maximum acceptable magnitude for SQI by substituting appropriate magnitudes in equation (10) above.

The Hanford Engineering Development Laboratory criterion weighted chips which contacted the ends of a pellet more severely in favor of rejection than chips between the ends. This weighting is achieved in the practice of this invention by multiplying F for an end chip by a factor $\gamma$ where $\gamma>1$.

Very small but evenly distributed flaws are likely to have little effect on pellet performance so long as the total flawed area is small with respect to the total pellet surface area. But when the ratio becomes large the average temperature of the remaining surface must climb. This requires that a maximum allowable flawed area criterion should be applied. $A_{max}$ is established at 10% of the nominal pellet surface area. For a typical pellet this is $$10\% \ 2\pi r l = 2\pi \left(\frac{.1945}{2}\right)(.2425) = .0148 \text{ square inches}$$

Flaws which are so small that they constitute surface roughness have no appreciable effect on heat transfer and are of no interest in evaluation of pellets for flaws. The threshold area below which flaws are of no consequence is defined as factor T, for example 0.000324 square inch.

The algorithm shown in FIG. 8 presents the analysis carried out by computer 105 pursuant to its program based on the above discussion. It is assumed that a pellet has been scanned and the crude or raw data entered in the memory of the computer. The computer computes the flaw quality index, FQI, of each flaw and sums the FQI's to derive a pellet surface quality index which is evaluated. For the first flaw the answer to "Is last flaw analyzed?" is "No.". The area A of the flaw is computed. If $A<T$, T being the maximum ignorable flaw area, further analysis of that flaw is aborted. If $A>T$, the process continues. For the first flaw, the area of the first flaw is the total. The perimeter P is computed and $S=4\pi A/P^2$ is computed. If $S>0.3$, and $A>0.0006$ in$^2$, the pellet is rejected for an unacceptable fissure. If not, the flaw quality index $$F = S^q P^2 = (1-S^q)A$$

is computed. In the equation for F, q is an empirically determined magnitude, P is the perimeter and A the area of a flaw. If the current flaw touches the end of a pellet the value of F is modified by multiplying F by γ. γ is an empirically determined factor usually greater than 1. SQI is the quality factor which was determined by adding Fs for flaws which were analyzed earlier. For the first flaw the F is adopted as SQI. If at this point SQI>SQI LIMIT, the acceptable limit, the pellet is rejected. If SQI<SQI LIMIT the above described process is repeated with F reset to 0. The F for the second flaw is detected and the new F is added to the first SQI. If now SQI<SQI LIMIT, the above process is repeated. All flaws for the pellet are analyzed in this way. The following are causes for pellet rejection:

1. The sum of the flaw areas which exceed T are greater than AMAX;
2. A flaw having a shape factor less than or equal to 0.3 and an area greater than T and also 0.0006 square inch;
3. A surface quality index greater than SQI LIMIT.

Otherwise, the pellet is acceptable.

While a preferred embodiment of this invention has been disclosed herein, many modifications thereof are feasible. For example, instead of being scanned by a light beam, the pellets could be scanned by a sonar beam or by a magnetic field or a photograph of the pellet could be analyzed by a densitometer. This invention should not be restricted except insofar as is necessitated by the spirit of the prior art.

We claim:

1. The method of inspecting fuel pellets for a nuclear reactor for flaws to determine if the shapes and the extents of the totality of the flaws in each pellet exceed predetermined maximum acceptable shape and extent, the said method including determining the area and perimeter of each flaw in the surface of said pellet to determine for each flaw a flaw quality index, dependent on each area and perimeter, summing the flaw quality indexes from all flaws in the surface of said pellet to derive a surface-quality index, and evaluating said pellet based on its surface-quality index by comparing said index with the index corresponding to said acceptable shape and extent.

2. The method of claim 1 wherein the determination of the flaw quality index, herein called F, for each flaw is varied in dependence upon the shape of said flaw.

3. The method of claim 2 wherein F for each flaw is varied in accordance with the equation:

$$F = S^q P^2 + (1-S^q)A$$

wherein

S is a factor governed by the shape of said flaw,
P is the perimeter of said flaw,
A is the area of said flaw, and
q is a correction quantity greater than 1 adopted to achieve desired variations of F as a function of length and width of a flaw, S being 1 for a circular flaw and 0 for a crack.

4. The method of claim 3 where:

$$S = (4\pi A)/P^2$$

where
S is the shape factor of a flaw,
A is the area of a flaw,
P is the perimeter of a flaw.

5. Apparatus for inspecting fuel pellets for a nuclear reactor including a roller stand, the said roller stand having rollers providing between them a seat for each of said pellets, and a first drive for rotating said rollers, transfer means for depositing pellets one-by-one on said seat, each deposited pellet being rotated by the rotation of the rollers forming said seat, a light source, optical means cooperative with said source for projecting a light beam on each pellet in said seat, said optical means including a multiple-sided prism and a second drive for rotating said prism to cause said light beam to scan said pellet in said seat, means connected to said first and second drives for synchronizing said drives, pellet sorting means, and means connected to said sorting means, responsive to the resulting light emitted by said pellet in said seat for sorting said pellet in accordance with its properties as manifested by the resulting emitted light.

6. The apparatus of claim 5 wherein the roller motor is energized from an alternating current commercial supply and the prism motor is energized by electrical current produced by a voltage-controlled oscillator, the said apparatus also including a phase detector and means connecting said commercial supply and the output of said oscillator to said phase detector to derive from said phase detector resulting synchronizing voltage, and means impressing said synchronizing voltage on said voltage-control oscillator to maintain the current supplied to the prism motor in synchronism with the current supplied to the roller motor.

7. In apparatus for inspecting fuel pellets for a nuclear reactor for flaws, each of said pellets in its turn being disposed in a pellet seat for inspection; an optical system comprising means, including a source of light, for producing a light beam, a prism interposed in said light beam, means connected to said prism for rotating said prism to scan said pellet with said light beam along a direction generally parallel to the axis of said pellet, a first cylindrical lens interposed in said light beam between said source and said prism for converging said beam to a line image generally perpendicular to the axis of said pellet at a point in said light beam just beyond said prism, a second cylindrical lens interposed between said prism and said pellet seat for converging said beam to a line on the surface of said pellet, generally parallel to the axis of said pellet, and a third cylindrical lens interposed between said prism and said pellet for focusing said line image on said surface of said pellet.

8. The optical system of claim 7 including a grating displaced from said pellet and a beam splitter interposed in said beam between the lenses and the pellet for deriving from said beam herein called the main beam, a branch beam at an angle to the main beam from which it is derived, said branch beam being incident on said grating.

9. The optical system of claim 7 wherein the third cylindrical lens is interposed between the second cylindrical lens and the pellet.

10. The optical system of claim 9 wherein the optical distance along the axis of the branch beam from the beam splitter to the grating is substantially equal to the optical distance along the axis of the main beam from the beam splitter to the surface of the pellet, whereby the branch beam is focused on the grating.

11. The method of inspecting fuel pellets for a nuclear reactor for flaws to determine if the shapes and extents of the totality of the flaws in each pellet exceed a predetermined maximum acceptable shape and extent, the said method including scanning elemental areas of the surface of each pellet with a beam of light, responsive to the resulting light reflected by said pellet, determining the shape and surface dimensions of each flaw in the surface of said pellet to determine for each flaw a flaw quality index, dependent on its shape and said surface dimensions, said surface dimensions being evaluated with each flaw assumed to have the contour and surface of a plane curve on the surface of said pellet, summing the flaw quality indexes from all flaws in the surface of said pellet to derive a surface-quality index, and evaluating said pellet based on its surface-quality index and comparing said surface-quality index with the surface-quality index corresponding to said acceptable shape and extent.

12. The method of claim 11 wherein each pellet is spun during the scanning.

13. The method of claim 12 wherein each pellet is scanned at a high repetitive rate compared to the angular velocity of the scanning.

* * * * *